US010821114B2

(12) United States Patent
Karaboga et al.

(10) Patent No.: US 10,821,114 B2
(45) Date of Patent: Nov. 3, 2020

(54) DERIVATIVES OF CEPHALOSPORIN FOR TREATING CANCER

(71) Applicants: INSTITUT CURIE, Paris (FR); HARMONIC PHARMA, Villers les Nancy (FR)

(72) Inventors: Arnaud Sinan Karaboga, Schiltigheim (FR); Violeta Isabel Perez-Nueno, Viladecans-Barcelona (ES); Michel Souchet, Gif sur Yvette (FR); Didier Decaudin, Paris (FR)

(73) Assignees: INSTITUT CURIE, Paris (FR); HARMONIC PHARMA, Villers les Nancy (FR)

( * ) Notice: Subject to any disclaimer, the term of this patent is extended or adjusted under 35 U.S.C. 154(b) by 322 days.

(21) Appl. No.: 15/301,462

(22) PCT Filed: Apr. 2, 2015

(86) PCT No.: PCT/EP2015/057310
§ 371 (c)(1),
(2) Date: Oct. 3, 2016

(87) PCT Pub. No.: WO2015/150516
PCT Pub. Date: Oct. 8, 2015

(65) Prior Publication Data
US 2017/0119784 A1   May 4, 2017

(30) Foreign Application Priority Data
Apr. 3, 2014 (EP) .................................. 14305487

(51) Int. Cl.
A61K 31/545 (2006.01)
A61K 45/06 (2006.01)
A61K 47/32 (2006.01)

(52) U.S. Cl.
CPC ............ *A61K 31/545* (2013.01); *A61K 45/06* (2013.01); *A61K 47/32* (2013.01)

(58) Field of Classification Search
CPC .............................. A61K 31/545; A61P 35/00
See application file for complete search history.

(56) References Cited

U.S. PATENT DOCUMENTS

| 2009/0274773 A1* | 11/2009 | Green | A61K 31/7068 424/649 |
| 2014/0107092 A1* | 4/2014 | Meyerson | C12Q 1/689 514/196 |

FOREIGN PATENT DOCUMENTS

| CN | 101319246 | 12/2008 |
| JP | 2002 316991 | 10/2002 |
| JP | 2012 509874 | 4/2012 |
| KR | 2010 0112672 | 10/2010 |
| WO | WO 02/096430 | 12/2002 |
| WO | WO 2006/069449 | 7/2006 |
| WO | WO 2007/013043 | 2/2007 |
| WO | WO 2009/149149 | 12/2009 |
| WO | WO 2010/065079 | 6/2010 |

OTHER PUBLICATIONS

Domanska, U. M. et al. "A review on CXCR4/CXCL12 axis in oncology: No place to hide" *European Journal of Cancer*, Jan. 2013, pp. 219-230, vol. 49, No. 1.
Li, X. et al. "Ceftriaxone, an FDA-approved cephalosporin antibiotic suppresses lung cancer growth by targeting Aurora B" *Carcinogenesis*, Dec. 2012, pp. 2548-2557, vol. 33, No. 12.
Oler, A. "Endogenous Cytotoxicity of Cephalosporins" *Federation of American Society for Experimental Biology*, Jan. 1, 1992, p. A1619 (3951), vol. 6, No. 5.
Written Opinion in International Application No. PCT/EP2015/057310, dated May 11, 2015, pp. 1-6.
Naito, T. et al. "Synthesis and Structure-Activity Relationships of a New Oral Cephalosporin, BMY-28100 and Related Compounds" *The Journal of Antibiotics*, Jul. 1987, pp. 991-1005, vol. XL, No. 7.

\* cited by examiner

*Primary Examiner* — James D. Anderson
(74) *Attorney, Agent, or Firm* — Saliwanchik, Lloyd & Eisenschenk

(57) ABSTRACT

The present invention relates to a new class of cephalosporin derivatives of formula (I), notably having CXCR4 receptor antagonist effect, useful as a therapeutic agent for treating cancer, in particular for treating breast cancer, lung cancer and uveal melanoma. The invention further relates to a pharmaceutical composition comprising a compound of formula (I) and an additional antitumor drug for treating cancer.

15 Claims, 3 Drawing Sheets

Day after start of treatment (d)

Days after start of treatment (d)

DERIVATIVES OF CEPHALOSPORIN FOR TREATING CANCER

CROSS-REFERENCE TO RELATED APPLICATION

Figure 1:
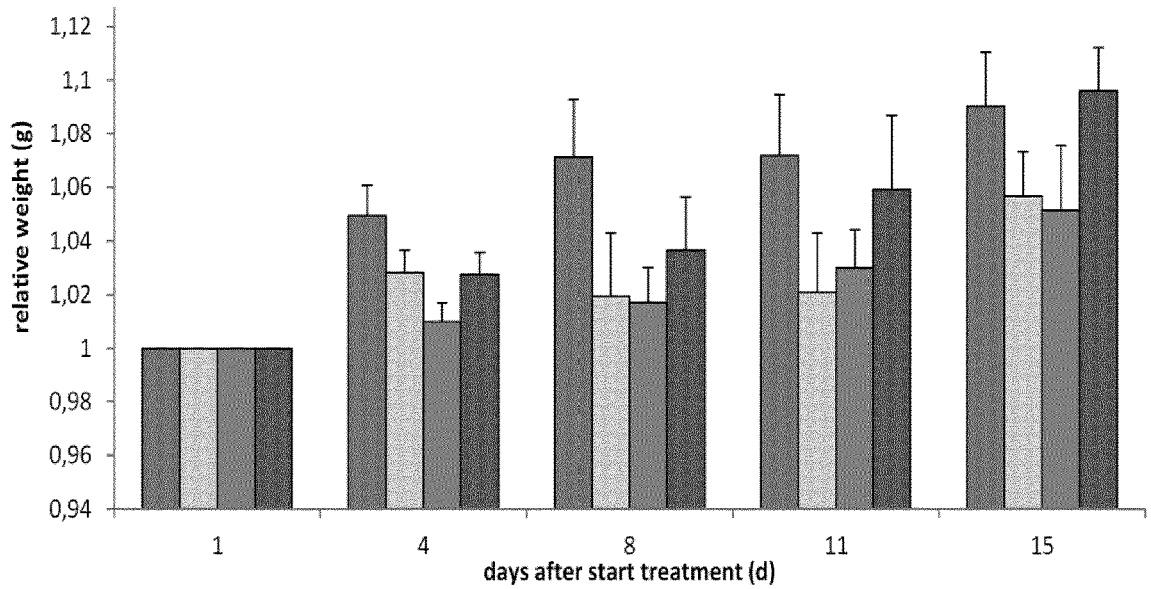

This application is the U.S. national stage application of International Patent Application No. PCT/EP2015/057310, filed Apr. 2, 2015.

FIELD OF THE INVENTION

The present invention relates to the field of medicine, in particular the use of CXCR4 receptor antagonists in the treatment of cancer.

BACKGROUND OF THE INVENTION

Classical antitumor chemotherapies induce cell death through DNA damage by taking advantage of the proliferative behavior of cancer cells. More recent therapeutic approaches relate, rather, to the interaction of cancer cells with their microenvironment, which occurs through chemokine receptors and their ligands (Domanska et al.: European Journal of Cancer, 2013, 49, 219-230). One important and representative chemokine-receptor couple is the chemokine ligand CXCL12 and its receptor CXCR4. CXCR4/CXCL12 is involved in proliferation of primary tumors, migration of tumor cells and establishment of metastases. Therefore, CXCL12/CXCR4 appears to be an attractive therapeutic approach and their interaction can be disrupted by CXCR4 antagonists. Several CXCR4 inhibitors have already been approved for cancer treatment, namely AMD3100 (Mozobil, plerixafor) and CTCE-9908, alone or in combination with conventional chemotherapy. In particular, CXCR4 antagonists have been demonstrated to be interesting drugs for sensitizing tumor cells to chemotherapy. Several other CXCR4 antagonists are currently being investigated in clinical trials. Therefore, any new CXCR4 antagonist is of great interest for developing antitumor treatments.

Otherwise, independent of the above therapeutic strategy, others have suggested the use of cephalosporins for treating cancers.

For instance, Barker et al. have reported, in WO 02/099430, the use of cephalosporin derivatives as potential anti-cancer agents. These derivatives have a weak antibiotic activity and have been designed to inhibit the complex formation of β-catenin and LEF/TCF, the inhibitory activity supporting their use as antitumor drug. A large number of derivatives have been prepared and tested for their capacity of inhibiting the complex formation. There is no data regarding a potential activity as an antitumor drug. Most of the derivatives disclosed by Barker et al. may be classified in three classes according to the definitions of the V and X substituents as represented in formula (A) below:

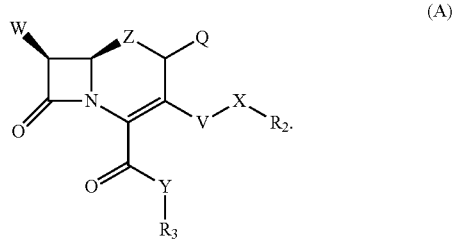

(A)

V and X may form a methyl acetate substituent, a methyl substituent or a sulfur-derived substituent, thereby defining each class of cephalosporin derivatives.

Li et al. (Carcinogenesis, 2012, 33, 2548-2557) have also reported that a third-generation cephalosporin known as Ceftriaxone suppresses lung cancer growth by targeting Aurora B. Ceftriaxone is substituted by a sulfur-derived substituent at position 3 of the cephalosporin core and of formula (B):

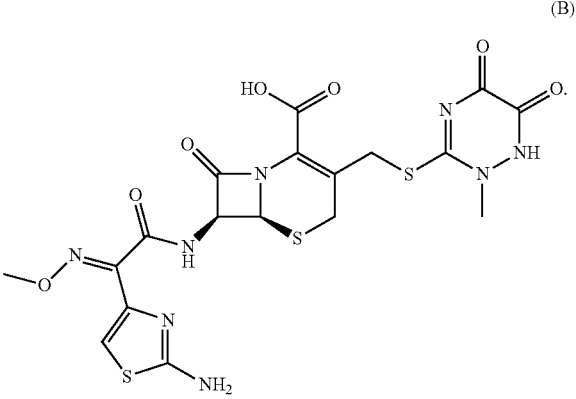 [SMILES: CO/N=C(/C(=O)N[C@H]1C(=O)N2C(C(=O)O)=C(CSc3nc(=O)c(=O)[nH]n3C)CS[C@@H]12)c1csc(N)n1]

(B)

However, there is still a need for developing new drugs and discovering new targets for treating cancer in order to improve the treatments given to the patients in need thereof.

SUMMARY OF THE INVENTION

In this context, the inventors surprisingly demonstrated and identified that a cephalosporin derivative represented by the formula (I) below is useful for treating cancer.

The present invention relates to compounds of formula (I):

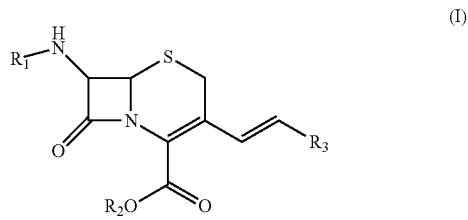

(I)

wherein:
$R_1$ represents:
  a hydrogen atom, or
  a —CO—$R_4$ unit or a —CO$_2$—$R_4$ unit wherein $R_4$ represents a radical ($C_1$-$C_{10}$)alkyl, ($C_2$-$C_{10}$)alkylene, ($C_3$-$C_{14}$)cycloalkyl, heterocycloalkyl, aryl, heteroaryl, ($C_1$-$C_6$)alkyl-($C_3$-$C_{14}$)cycloalkyl, ($C_1$-$C_6$)alkyl-heterocycloalkyl, ($C_1$-$C_6$)alkyl-($C_3$-$C_{14}$)cycloalkyloxy, ($C_1$-$C_6$)alkyl-heterocycloalkyloxy, ($C_1$-$C_6$)alkyl-aryl, ($C_1$-$C_6$)alkyl-aryloxy, ($C_1$-$C_6$)alkyl-heteroaryl, or ($C_1$-$C_6$)alkyl-heteroaryloxy, said radicals being optionally substituted by at least one ($C_1$-$C_6$)alkyl group, one hydroxy group, one ketone, one ($C_1$-$C_6$)alkoxy group, one carboxylic acid group eventually substituted by a ($C_1$-$C_6$)alkyl group, one —NR$_5$R$_6$ unit wherein $R_5$ and $R_6$ represent a hydrogen atom or a ($C_1$-$C_6$)alkyl group, one halogen atom, one cyano group, or one nitro group;

$R_2$ represents a hydrogen atom or a chain ($C_1$-$C_6$)alkyl; and $R_3$ represents a hydrogen atom, a chain ($C_1$-$C_6$)alkyl, or ($C_2$-$C_6$)alkylene, said chains being optionally substituted by at least one ($C_1$-$C_6$)alkyl group, one hydroxy group, one —O—CO—($C_1$-$C_6$)alkyl unit, one ketone, one carboxylic acid group eventually substituted by a ($C_1$-$C_6$)alkyl group, one —$NR_5R_6$ unit wherein $R_5$ and $R_6$ represent H or a ($C_1$-$C_6$)alkyl group, one halogen atom, one cyano group or one nitro group;

or one of its pharmaceutically acceptable salts, for use in the treatment of cancer.

In a particular embodiment of the compound of formula (I) as defined above, $R_2$ represents a hydrogen atom.

In another particular embodiment of the compound of formula (I) as defined above, $R_3$ represents a hydrogen atom or a chain ($C_1$-$C_6$)alkyl. Advantageously, $R_3$ is a hydrogen atom or a methyl.

In a further particular embodiment of the compound of formula (I) as defined above, $R_1$ represents:

a hydrogen atom, or a —CO—$R_4$ unit wherein $R_4$ represents a radical ($C_1$-$C_6$) alkyl, aryl, heteroaryl, ($C_1$-$C_6$)alkyl-aryl, or ($C_1$-$C_6$) alkyl-heteroaryl, said radicals being optionally substituted by at least one ($C_1$-$C_6$)alkyl group, one hydroxy group, one ($C_1$-$C_6$)alkoxy group, one carboxylic acid group eventually substituted by a ($C_1$-$C_6$)alkyl group, one —$NR_5R_6$ unit wherein $R_5$ and $R_6$ are such as defined above, one halogen atom, or one cyano group.

Preferably, $R_1$ represents:

a hydrogen atom, or a —CO—$R_4$ unit wherein $R_4$ represents:

a methylaryl, preferably a methylphenyl, a methylphenol or a methylthiophene, eventually substituted by an amino, methyl or hydroxy group, an amino acid radical selected from the group consisting of alaninyl, glycinyl, histidinyl, isoleucinyl, leucinyl, phenylalaninyl, serinyl, threoninyl, tyrosinyl, valine and their derivatives, preferably tyrosinyl or one of its derivatives, an aryl, preferably a phenyl or an imidazolyl, eventually substituted by at least one methyl group or one cyano group; or a propyl, eventually substituted by one carboxylic acid group.

More preferably, $R_1$ represents a hydrogen atom or tyrosinyl.

In a very particular aspect, the compound is selected from the group consisting of:

7-(2-amino-2-(4-hydroxyphenyl)acetamido)-8-oxo-3-(prop-1-enyl)-5-thia-1-azabicyclo[4.2.0]oct-2-ene-carboxylic acid;

7-amino-8-oxo-3-vinyl-5-thia-1-azabicyclo[4.2.0]oct-2-ene-carboxylic acid; and 8-oxo-7-(2-phenylacetamido)-3-vinyl-5-thia-1-azabicyclo [4.2.0]oct-2-ene-carboxylic acid.

More preferably, the compound is selected from the group consisting of:

7-(2-amino-2-(4-hydroxyphenyl)acetamido)-8-oxo-3-(prop-1-enyl)-5-thia-1-azabicyclo[4.2.0]oct-2-ene-carboxylic acid; and 7-amino-8-oxo-3-vinyl-5-thia-1-azabicyclo[4.2.0]oct-2-ene-carboxylic acid.

Particularly, the compounds of the present invention have a CXCR4 antagonist effect.

In a particular embodiment, the compounds of the present invention are formulated in an extended-release, controlled-release or sustained-release pharmaceutical composition. Preferably, the extended-release, controlled-release, or sustained-release pharmaceutical composition comprises one or more carbomers.

Preferably, the compounds of the present invention are used for treating solid tumors, especially breast cancer, lung cancer or melanoma, particularly uveal melanoma.

The present invention further relates to a pharmaceutical composition comprising as active ingredients one compound of the formula (I) as defined above and at least one additional antitumor drug, for use in the treatment of cancer, preferably solid tumors, especially breast cancer, lung cancer or melanoma, particularly uveal melanoma.

Preferably, the additional antitumor drug is selected from the group consisting of an inhibitor of topoisomerases I or II, a DNA alkylating agent, an anti-metabolic agent, a targeted agent such as a kinase inhibitor, a therapeutic antibody designed to mediate cytotoxicity against the cancer cells or to modulate one of their key biological functions, and/or an anti-EGFR (epithelial growth factor receptor) agent. The DNA alkylating agent is preferably selected from the group consisting of Cisplatin, Carboplatine, Oxaliplatine, Fotemustine and Dacarbazine, and more preferably is Cisplatin, Fotemustine or Dacarbazine. The antimitotic agent is preferably Docetaxel or Paclitaxel, and more preferably Docetaxel. The anti-EGFR agent can be selected from among Erlotinib, Cetuximab, Gefitinib, Zalutumumab, Panitumumab, Nimotuzumab, Matuzumab, and Lapatinib, preferably Cetuximab.

Particularly, the compounds or the pharmaceutical composition of the present invention can be used for treating cancer in combination with radiotherapy, hyperthermia, hormonotherapies and/or other antitumor therapies, optionally before, simultaneously with and/or after surgery.

The present invention further relates to a kit comprising (a) a compound of the present invention and (b) an additional antitumor drug as a combined preparation for simultaneous, separate or sequential use, for treating cancer. Advantageously, the kit is used for the treatment of solid tumors, especially breast cancer, lung cancer or melanoma, in particular uveal melanoma.

DETAILED DESCRIPTION OF THE INVENTION

The inventors identified a new use of cephalosporin derivatives of formula (I):

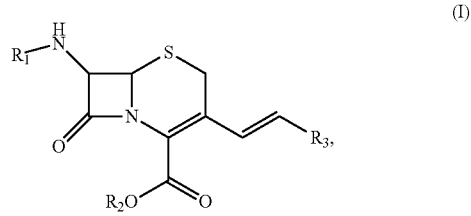

having a therapeutic interest for treating cancer as an inhibitor of the CXCR4 receptor. The inventors, surprisingly, discovered that cephalosporin compounds substituted by an alkylene chain at position 3 of the cephalosporin core have a significant CXCR4 inhibitor activity.

In particular, a better CXCR4 inhibition profile is surprisingly observed with compounds of formula (I) of the present invention wherein $R_3$ represents a methyl group or a hydrogen atom compared to the compounds disclosed by WO 02/099430.

Accordingly, the present invention relates to a compound of formula (I), particularly having a CXCR4 receptor antagonist activity, for use for treating cancer:

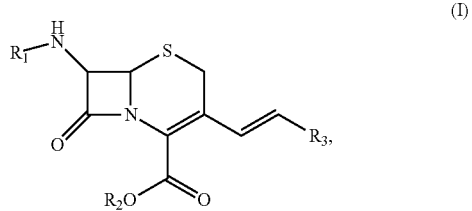

(I)

wherein:
R$_1$ represents:
  a hydrogen atom, or
  a —CO—R$_4$ unit or a —CO$_2$—R$_4$ unit wherein R$_4$ represents a radical (C$_1$-C$_{10}$)alkyl, (C$_2$-C$_{10}$)alkylene, (C$_3$-C$_{14}$)cycloalkyl, heterocycloalkyl, aryl, heteroaryl, (C$_1$-C$_6$)alkyl-(C$_3$-C$_{14}$)cycloalkyl, (C$_1$-C$_6$)alkyl-heterocycloalkyl, (C$_1$-C$_6$)alkyl-(C$_3$-C$_{14}$)cycloalkyloxy, (C$_1$-C$_6$)alkyl-heterocycloalkyloxy, (C$_1$-C$_6$)alkyl-aryl, (C$_1$-C$_6$)alkyl-aryloxy, (C$_1$-C$_6$)alkyl-heteroaryl, or (C$_1$-C$_6$)alkyl-heteroaryloxy, said chains being optionally substituted by at least one (C$_1$-C$_6$)alkyl group, one hydroxy group, one ketone, one (C$_1$-C$_6$)alkoxy group, one carboxylic acid group eventually substituted by a (C$_1$-C$_6$)alkyl group, one —NR$_5$R$_6$ unit wherein R$_5$ and R$_6$ represent a hydrogen atom or a (C$_1$-C$_6$)alkyl group, one halogen atom, one cyano group, or one nitro group;
R$_2$ represents a hydrogen atom or a chain (C$_1$-C$_6$)alkyl; and
R$_3$ represents a hydrogen atom, a chain (C$_1$-C$_6$)alkyl, or (C$_2$-C$_6$)alkylene, said chains being optionally substituted by at least one (C$_1$-C$_6$)alkyl group, one hydroxy group, one —O—CO—(C$_1$-C$_6$)alkyl unit, one ketone, one carboxylic acid group eventually substituted by a (C$_1$-C$_6$)alkyl group, one —NR$_5$R$_6$ unit wherein R$_5$ and R$_6$ represent H or a (C$_1$-C$_6$)alkyl group, one halogen atom, one cyano group or one nitro group;
or one of its pharmaceutically acceptable salts, for use in the treatment of cancer.

According to the present invention, the terms below have the following meanings: The terms mentioned herein with prefixes such as C$_1$-C$_3$, C$_1$-C$_6$, C$_1$-C$_{10}$, C$_2$-C$_{10}$, or C$_3$-C$_{14}$ can also be used with lower numbers of carbon atoms such as C$_1$-C$_2$, C$_1$-C$_5$, C$_1$-C$_9$, C$_2$-C$_9$, or C$_3$-C$_{13}$. If, for example, the term C$_1$-C$_3$ is used, it means that the corresponding hydrocarbon chain may comprise from 1 to 3 carbon atoms, especially 1, 2 or 3 carbon atoms. If, for example, the term C$_1$-C$_6$ is used, it means that the corresponding hydrocarbon chain may comprise from 1 to 6 carbon atoms, especially 1, 2, 3, 4, 5 or 6 carbon atoms. If, for example, the term C$_2$-C$_{10}$ is used, it means that the corresponding hydrocarbon chain may comprise from 2 to 10 carbon atoms, especially 2, 3, 4, 5, 6, 7, 8, 9 or 10 carbon atoms.

The term "alkyl" refers to a saturated, linear or branched aliphatic group. The term "(C$_1$-C$_3$)alkyl" more specifically means methyl (also called "Me"), ethyl (also called "Et"), propyl, or isopropyl. The term "(C$_1$-C$_6$)alkyl" more specifically means methyl, ethyl, propyl, isopropyl, butyl, isobutyl, tert-butyl, pentyl or hexyl.

The term "alkylene" refers to an unsaturated linear or branched aliphatic group.

The term "cycloalkyl" refers to a saturated aliphatic cycle, substituted or not substituted, corresponding to a mono- or poly-cyclic group.

The term "heterocycloalkyl" refers to a cycloalkyl as above defined and comprising at least one heteroatom such as a nitrogen, oxygen or sulphur atom.

The term "aryl" is mono- or bi-cyclic aromatic hydrocarbons having from 6 to 12 carbon atoms, optionally substituted. Aryl may be a phenyl (also called "Ph"), biphenyl or naphthyl. In a preferred embodiment, the aryl is a phenyl.

The term "heteroaryl" as used herein corresponds to an aromatic, mono- or poly-cyclic group comprising between 5 and 14 atoms and comprising at least one heteroatom such as a nitrogen, oxygen or sulphur atom. Examples of such mono- and poly-cyclic heteroaryl groups may be: pyridyl, dihydroxypyridyl, thiazolyl, thiophenyl, furanyl, azocinyl, pyranyl, pyrrolyl, pyrazolyl, imidazolyl, triazolyl, tetrazolyl, benzofuranyl, thianaphthalenyl, indolyl, indolenyl, quinolinyl, isoquinolinyl, benzimidazolyl, pyrrolinyl, tetrahydroquinolinyl, tetrahydroisoquinolinyl, triazinyl, 6H-1,2,5-thiadiazinyl, 2H,6H-1,5,2-dithiazinyl, thianthrenyl, isobenzofuranyl, chromenyl, xanthenyl, phenoxanthinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, P-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, dihydropyridyl, pyrimidinyl, pyrazinyl, s-triazinyl, oxazolyl, and thiofuranyl. In a preferred embodiment, heteroaryl is an aromatic monocyclic comprising 5 or 6 atoms and comprising at least one heteroatom such as nitrogen, oxygen or sulphur atom. Preferably, heteroaryl is pyridyl, thiazolyl, furanyl, pyranyl, pyrrolyl, imidazolyl, tetrazolyl, benzofuranyl, pyrrolinyl, triazinyl, pyrazinyl, pyridazinyl, triazolyl or tetrazolyl. More preferably, heteroaryl is imidazolyl.

The terms "alkoxy" or "alkyloxy" and "cycloalkyloxy" correspond to the alkyl or cycloalkyl groups defined hereinabove bonded to the molecule by an —O— (ether) bond. (C$_1$-C$_6$)alkoxy includes methoxy, ethoxy, propyloxy, isopropyloxy, butyloxy, isobutyloxy, tert-butyloxy, pentyloxy and hexyloxy.

The term "halogen" corresponds to a fluorine, chlorine, bromine, or iodine atom, preferably a chlorine or a fluorine.

The expression "substituted by at least" or "substituted by" means that the radical is substituted by one or several groups from the list.

The pharmaceutically acceptable salts include inorganic as well as organic acid salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically acceptable inorganic or organic acid addition salts include the pharmaceutically acceptable salts listed in J. Pharm. Sci. 1977, 66, 2, and in Handbook of Pharmaceutical Salts: Properties, Selection, and Use edited by P. Heinrich Stahl and Camille G. Wermuth 2002. In a preferred embodiment, the salt is selected from the group consisting of maleate, chlorhydrate, bromhydrate, and methanesulfonate.

In a particular embodiment, the present invention relates to compounds of formula (I) wherein $R_2$ represents a hydrogen atom thereby forming a carboxylic acid function (—COOH) at position 2 of the cephalosporin core.

In a particular embodiment, $R_3$ represents a hydrogen or a $(C_1\text{-}C_6)$alkyl chain, preferably a methyl group, thereby corresponding to a low steric hindrance substituent at position 3 of the cephalosporin core, such as $(C_2\text{-}C_8)$alkylene chain for instance ethylene, propylene, butylene, pentylene, hexylene, heptylene or octylene. The $(C_2\text{-}C_8)$ chain may optionally be substituted by at least one $(C_1\text{-}C_3)$alkyl group, one hydroxy group, one ketone, one carboxylic acid group eventually substituted by a $(C_1\text{-}C_3)$alkyl group, one —$NR_5R_6$ unit wherein $R_5$ and $R_6$ represent H or a $(C_1\text{-}C_3)$ alkyl group, one halogen atom, one cyano group or one nitro group.

In a particular embodiment, $R_1$ represents:
a hydrogen atom, or
a —CO—$R_4$ unit wherein $R_4$ represents a radical $(C_1\text{-}C_6)$ alkyl, aryl, heteroaryl, $(C_1\text{-}C_6)$alkyl-aryl, $(C_1\text{-}C_6)$alkyl-heteroaryl, said radicals being optionally substituted by at least one $(C_1\text{-}C_6)$alkyl group, one hydroxy group, one $(C_1\text{-}C_6)$alkoxy group, one carboxylic acid group eventually substituted by a $(C_1\text{-}C_6)$alkyl group, one —$NR_5R_6$ unit wherein $R_5$ and $R_6$ are such as defined above, one halogen atom, or one cyano group.

Typically, $R_1$ represents a —CO—$R_4$ unit and $R_4$ represents a radical $(C_1\text{-}C_6)$alkyl or a $(C_1\text{-}C_6)$alkyl-aryl substituted by an amino group allowing to form any amino acid known to the skilled person in the art. According to a preferred embodiment of the invention, $R_1$ represents an amino acid chosen from among alanine, glycine, histidine, isoleucine, leucine, phenylalanine, serine, threonine, tyrosine or valine, preferably tyrosine, or one of its derivatives. The amino acid and its derivatives representing the substituent $R_1$ in the formula (I) of the invention may be of natural origin or may be synthesized without difficulty by a person skilled in the art, using the conventional techniques.

Preferably, $R_1$ represents:
a hydrogen atom, or
a —CO—$R_4$ unit wherein $R_4$ represents:
   a methylaryl, preferably a methylphenyl, a methylphenol or a methylthiophene, eventually substituted by an amino, methyl or a hydroxy group,
   an amino acid selected from the group consisting of alaninyl, glycinyl, histidinyl, isoleucinyl, leucinyl, phenylalaninyl, serinyl, threoninyl, tyrosinyl, valine and their derivatives, preferably tyrosinyl or one of its derivatives,
   an aryl, preferably a phenyl or an imidazolyl, eventually substituted by at least one methyl group or one cyano group, or
   a propyl, eventually substituted by one carboxylic acid group.

The amino acid can have L or D conformation. The tyrosinyl derivatives include α-methyl-tyrosinyl, dopa, m-tyrosinyl, 3-halogenotyrosinyl (e.g., iodo, bromo, fluoro, or chloro), 3,5-dihalogenotyrosinyl (e.g., diiodo, dibromo, difluoro, or dichloro, or any combination of iodo, bromo, fluoro, or chloro), N-hydroxyltyrosinyl, N,N-dihydroxytyrosinyl, 6-hydroxydopa, 6-halogenodopa, and 3-amino-3-(4-hydroxyphenyl)propanyl.

In a particular aspect, $R_1$ can be selected from the group consisting of amino, tyrosinyl, —CO—$(CH_2)_3$—COOH, —CO-phenyl-CN, —CO-dimethylimidazolyl, —CO-methylphenyl, —CO-hydroxymethylphenyl, —CO-dimethylphenyl, and —CO-methylthiophene.

More preferably, $R_1$ is hydrogen or tyrosinyl, in particular L-tyrosinyl or D-tyrosinyl, still more preferably D-tyrosinyl.

Advantageously, $R_1$, $R_2$, $R_3$ and $R_4$ are defined such as:
$R_1$ represents:
   a hydrogen atom, or
   a —CO—$R_4$ unit wherein $R_4$ represents:
      a methylaryl, preferably a methylphenyl, a methylphenol or a methylthiophene, eventually substituted by an amino, methyl or a hydroxy group,
      an amino acid selected from the group consisting of alaninyl, glycinyl, histidinyl, isoleucinyl, leucinyl, phenylalaninyl, serinyl, threoninyl, tyrosinyl, valine and their derivatives, preferably tyrosinyl or one of its derivatives,
      an aryl, preferably a phenyl or an imidazole, eventually substituted by at least one methyl group or one cyano group; or
      a propyl, eventually substituted by one carboxylic acid group;
$R_2$ represents a hydrogen atom; and
$R_3$ represents a hydrogen atom or a $(C_1\text{-}C_6)$alkyl chain, preferably a methyl.

The amino acid can have L or D conformation. The amino acid substituent is linked to the cephalosporin core by its carboxyl part. The tyrosinyl derivatives include α-methyl-tyrosinyl, dopa, m-tyrosinyl, 3-halogenotyrosinyl (e.g., iodo, bromo, fluoro, or chloro), 3,5-dihalogenotyrosinyl (e.g., diiodo, dibromo, difluoro, or dichloro, or any combination of iodo, bromo, fluoro, or chloro), N-hydroxyltyrosinyl, N,N-dihydroxytyrosinyl, 6-hydroxydopa, 6-halogenodopa, and 3-amino-3-(4-hydroxyphenyl)propanyl.

In a particular aspect, $R_1$ can be selected from the group consisting of amino, tyrosinyl, —CO—$(CH_2)_3$—COOH, —CO-phenyl-CN, —CO-dimethylimidazolyl, —CO-methylphenyl, —CO-hydroxymethylphenyl, —CO-dimethylphenyl, and —CO-methylthiophene.

More preferably, $R_1$ is hydrogen or tyrosinyl, in particular L-tyrosinyl or D-tyrosinyl, still more preferably D-tyrosinyl.

Among the compounds for treating cancer according to the present invention, the following list of compounds may be cited:
7-(2-amino-2-(4-hydroxyphenyl)acetamido)-8-oxo-3-(prop-1-enyl)-5-thia-1-azabicyclo[4.2.0]oct-2-ene-carboxylic acid;
7-amino-8-oxo-3-vinyl-5-thia-1-azabicyclo[4.2.0]oct-2-ene-carboxylic acid; and
8-oxo-7-(2-phenylacetamido)-3-vinyl-5-thia-1-azabicyclo[4.2.0]oct-2-ene-carboxylic acid.

Preferably, compounds are chosen from the group consisting of:
7-(2-amino-2-(4-hydroxyphenyl)acetamido)-8-oxo-3-(prop-1-enyl)-5-thia-1-azabicyclo[4.2.0]oct-2-ene-carboxylic acid; and
7-amino-8-oxo-3-vinyl-5-thia-1-azabicyclo[4.2.0]oct-2-ene-carboxylic acid.

The CXCR4 antagonist activity of the compounds can be assessed by any method available and known by the person skilled in the art (Zhou, Y. et al.: J. Biol. Chem., 2002, 227, 49481-87). In a particular aspect, the antagonist activity can be assessed as disclosed in detail in Example 1. Preferably, a compound is considered as having a significant CXCR4 antagonist activity when a percentage of inhibition of at least 20% is observed, preferably at least 25%, especially when using the method disclosed in Example 1.

The present invention also concerns:
- a pharmaceutical composition comprising a compound of formula (I) as defined above including any one of the disclosed embodiments, and a pharmaceutically acceptable carrier for treating or for use for treating cancer; and/or
- a compound of formula (I) as defined above including any one of the disclosed embodiments formulated in an extended-release, controlled-release or sustained-release pharmaceutical composition for treating or for use for treating cancer; and/or
- a pharmaceutical composition comprising a compound of formula (I) as defined above including any one of the disclosed embodiments, and an additional antitumor drug, for the treatment of cancer or for use in the treatment of cancer; and/or
- a compound of formula (I) or a pharmaceutical composition as defined above including any one of the disclosed embodiments, for treating cancer or for use for treating cancer in combination with radiotherapy, hyperthermia and/or other antitumor therapies, optionally before, simultaneously and/or after surgery (e.g., tumor resection); and/or
- a kit comprising (a) a compound of formula (I) as defined above including any one of the disclosed embodiments and (b) an additional antitumor drug as a combined preparation for simultaneous, separate or sequential use, for treating cancer or for use for treating cancer; and/or
- the use of a pharmaceutical composition as defined above or a compound of formula (I) as defined above including any one of the disclosed embodiments, for the manufacture of a medicament for the treatment of cancer; and/or
- a method for treating a cancer, in a subject in need thereof, comprising administering an effective amount of a compound of formula (I) as defined above or a pharmaceutical composition as defined above; optionally, the method further comprises radiotherapy, hyperthermia and/or other antitumor therapies, optionally surgery (e.g., tumor resection).

The term "cancer", as used herein, refers to the presence of cells possessing characteristics typical of cancer-causing cells, such as uncontrolled proliferation, immortality, metastatic potential, rapid growth and proliferation rate, and certain characteristic morphological features. The cancer may be solid tumors or hematopoietic tumors. Examples of cancer include, for example, leukemia, lymphoma, blastoma, carcinoma, melanoma and sarcoma. Preferably, the cancer is a solid tumor, for instance blastoma, carcinoma, melanoma and sarcoma. More particular examples of such cancers include chronic myeloid leukemia, acute lymphoblastic leukemia, Philadelphia chromosome positive acute lymphoblastic leukemia (Ph+ ALL), squamous cell carcinoma, lung cancer, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, osteosarcoma, pancreatic cancer, glioblastoma multiforme, cervical cancer, stomach cancer, bladder cancer, hepatoma, breast cancer, oesophagal cancer, colon carcinoma, head and neck cancer, gastric cancer, germ cell tumor, pediatric sarcoma, sinonasal natural killer, multiple myeloma, uveal melanoma, acute myelogenous leukemia (AML), chronic lymphocytic leukemia, mastocytosis and any symptom associated with mastocytosis. Preferably, the cancer is selected from the group consisting of a breast cancer, a lung cancer, a melanoma and a mutated KRAS and/or a mutated EGFR cancer. More preferably, the cancer is a mutated KRAS and/or a mutated EGFR breast cancer, lung cancer and a melanoma. In a very particular aspect, the breast cancer is preferably a triple-negative breast cancer (ER-, PR-, Her2-). In another very particular aspect, the lung cancer is preferably a non-small cell lung cancer (NSCLC), preferably a mutated KRAS and/or a mutated EGFR NSCLC cancer. In a further very particular aspect, the melanoma is an uveal melanoma, preferably with a mutated GNA11 or GNAQ. Alternatively, the melanoma is a melanoma with a mutated GNA11 or GNAQ.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease. More particularly, the treatment may reduce the development of tumors, reduce tumor burden, produce tumor regression in a mammalian host and/or prevent metastasis occurrence and cancer relapse.

By "effective amount" it is meant the quantity of the pharmaceutical composition of the invention which prevents, removes or reduces the deleterious effects of the treated disease in humans. It is understood that the administered dose may be adapted by those skilled in the art according to the patient, the pathology, the mode of administration, etc. For instance, the compounds of the invention may be used at a dose of 0.01 to 500 mg/kg of body weight/day. In a particular embodiment, the pharmaceutical composition according to the invention comprises 0.01 to 500 mg/kg of the compound of the invention, preferably between 0.1 and 500 mg/kg/day, more preferably 10 and 400 mg/kg/day. In a particular aspect, the compounds of the invention can be administered by oral route at a daily dose of between 0.1 and 500 mg/kg, preferably 10 and 400 mg/kg. They can be administered 4, 5, 6 or 7 days a week during 1, 2, 3, 4, 5, 6 or 7 weeks. Optionally, several treatment cycles can be performed, optionally with a break period between two treatment cycles, for instance of 1, 2, 3, 4 or 5 weeks.

The administration route can be topical, transdermal, oral, rectal, sublingual, intranasal, intrathecal, intratumoral or parenteral (including subcutaneous, intramuscular, intravenous and/or intradermal). Preferably, the administration route is parental, oral or topical. The pharmaceutical composition is adapted for one or several of the above-mentioned routes. The pharmaceutical composition, kit, product or combined preparation is preferably administered by injection or by intravenous infusion or suitable sterile solutions, or in the form of liquid or solid doses via the alimentary canal.

The pharmaceutical composition can be formulated as solutions in pharmaceutically compatible solvents or as emulsions, suspensions or dispersions in suitable pharmaceutical solvents or vehicles, or as pills, tablets or capsules that contain solid vehicles in a way known in the art. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations for rectal administration may be in the form of a suppository incorporating the active ingredient and carrier such as cocoa butter, or in the form of an enema. Formulations suitable for parenteral administration conveniently comprise a sterile oily or aqueous preparation of the active ingredient which is preferably isotonic with the blood of the recipient. Every such formulation can also contain other pharmaceutically compatible and nontoxic auxiliary agents, such as stabilizers, antioxidants, binders, dyes, emulsifiers or flavoring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

In a particular aspect of the invention, the compounds of the invention are formulated in an extended-release, controlled-release or sustained-release pharmaceutical composition. By extended-, controlled- or sustained-release is meant a release which is slower and steadier into the bloodstream then immediate release.

In this aspect, the pharmaceutical composition comprises at least one compound of the invention and any excipients suitable to an extended-, controlled- or sustained-release. A skilled person could easily adapt the nature and the quantity of such excipients in the extended-, controlled- or sustained-release pharmaceutical composition according to the desired pharmacokinetic.

Typical excipients for an extended-, controlled- or sustained-release are carbomers. WO 2005/030178 is herein incorporated by reference. Carbomers are acrylic acid polymers, crosslinked with polyalkenyl ethers making them soluble in water and are found to be compatible with the compounds of the invention. They can be used as a single carbomer or as a mixture of various grades of carbomers in order to modify the release of the compound of the invention. As an example, the commercially available Carbopol® Polymers such as Carbopol 971P and Carbopol 974P may be cited.

In a preferred embodiment, the extended-, controlled- or sustained-release pharmaceutical composition comprises a compound of the invention and one or more carbomers. Particularly, the carbomers or polymers are in a proportion of 0.1-50%, preferably 0.1-40%, by weight relative to the total weight of the composition.

The extended-, controlled- or sustained-release pharmaceutical composition may further comprise one or more of pharmaceutically acceptable excipients such as diluents and lubricants. Diluents include water-soluble and water-dispersible diluents. Examples of water-soluble diluents comprise without limitation lactose, mannitol, glucose, sorbitol, maltose, dextrates, dextrins and the like. Particularly, the water-soluble diluent is in a proportion of 5-20% by weight relative to the total weight of the composition. Examples of water-dispersible diluents comprise without limitation microcrystalline cellulose, starch, pre-gelatinized starch, magnesium aluminium silicates and the like. Particularly, the water-dispersible diluent is in a proportion of 5-20% by weight relative to the total weight of the composition. Lubricants include without limitation talc, stearic acid, magnesium stearate, colloidal silicon dioxide, calcium stearate, zinc stearate, hydrogenated vegetable oil and the like. Particularly, the lubricant is in a proportion of 0.2-5% by weight relative to the total weight of the composition.

In a preferred embodiment, the extended-, controlled- or sustained-release pharmaceutical composition comprises a compound of formula (I) as defined above and a mixture of carbomers, lactose, and magnesium stearate.

More preferably, the compound of formula (I) as defined above is present in an amount of at least 100 mg, preferably of at least 500 mg per dosage form, more preferably in the range of 600 mg to 2,000 mg per dosage form.

Examples of extended-, controlled- or sustained-release pharmaceutical compositions according to the invention are disclosed at examples 1-4 of WO 2005/030178 and are hereby incorporated by reference.

In addition, the compounds of the invention can be used in combination with at least one additional antitumor drug. The additional antitumor drug can be selected from the non-exhaustive list of antitumor agents consisting of an inhibitor of topoisomerases I or II, an anti-mitotic agent, a DNA alkylating agent, an agent causing crosslinking of DNA, an anti-metabolic agent, a targeted agent such as a kinase inhibitor and an anti-EGFR agent and/or a therapeutic antibody designed to mediate cytotoxicity against the cancer cells or to modulate one of their key biological functions.

Antimitotic agents include, but are not limited to, Paclitaxel, Docetaxel and analogs such as Larotaxel (also called XRP9881; Sanofi-Aventis), XRP6258 (Sanofi-Aventis), BMS-184476 (Bristol-Meyer-Squibb), BMS-188797 (Bristol-Meyer-Squibb), BMS-275183 (Bristol-Meyer-Squibb), Ortataxel (also called IDN 5109, BAY 59-8862 or SB-T-101131; Bristol-Meyer-Squibb), RPR 109881A (Bristol-Meyer-Squibb), RPR 116258 (Bristol-Meyer-Squibb), NBT-287 (TAPESTRY), PG-Paclitaxel (also called CT-2103, PPX, Paclitaxel Poliglumex, Paclitaxel Polyglutamate or Xyotax™), ABRAXANE® (also called Nab-Paclitaxel; ABRAXIS BIOSCIENCE), Tesetaxel (also called DJ-927), IDN 5390 (INDENA), Taxoprexin (also called Docosahexanoic acid-Paclitaxel; PROTARGA), DHA-Paclitaxel (also called Taxoprexin®), and MAC-321 (WYETH). Preferably, antimitotic agents are Docetaxel, or Paclitaxel, and is more preferably Docetaxel.

Inhibitors of topoisomerases I and/or II include, but are not limited to, etoposide, topotecan, camptothecin, irinotecan, amsacrine, intoplicin, and anthracyclines such as Doxorubicin, Epirubicin, Daunorubicin, Idarubicin and Mitoxantrone. Inhibitors of topoisomerases I and II include, but are not limited to, Intoplicin.

The additional antitumor agent can be alkylating agents including, without limitation, nitrogen mustards, ethylenimine derivatives, alkyl sulfonates, nitrosoureas, metal salts and triazenes. Non-exhaustive examples thereof include Uracil mustard, Chlormethine, Cyclophosphamide (CY-TOXAN®), Ifosfamide, Melphalan, Chlorambucil, Pipobroman, Triethylenemelamine, Triethylenethiophosphoramine, Busulfan, Carmustine, Lomustine, Cisplatin, Carboplatin, Fotemustine, Oxaliplatin, Thiotepa, Streptozocin, Dacarbazine, and Temozolomide. In a preferred embodiment, the DNA alkylating agent is preferably Cisplatin, Fotemustine or Dacarbazine.

Anti-metabolic agents block the enzymes responsible for nucleic acid synthesis or become incorporated into DNA, which produces an incorrect genetic code and leads to apoptosis. Non-exhaustive examples thereof include, without limitation, folic acid antagonists, pyrimidine analogs, purine analogs and adenosine deaminase inhibitors, and more particularly Methotrexate, Floxuridine, Cytarabine, 6-Mercaptopurine, 6-Thioguanine, Fludarabine phosphate, Pentostatine, 5-Fluorouracil, Gemcitabine and Capecitabine.

The additional anti-tumor agent can also be a targeted agent, in particular a kinase inhibitor. The kinase may be selected from the group consisting of intracellular tyrosine or serine/threonine kinases, receptors tyrosine or serine/theonine kinase. For instance, the agents may have ability to inhibit angiogenesis based on the inhibitory activities of VEGFR and PDGFR kinases. In particular, the targeted agent can be selected from among the multiple kinase inhibitor drugs which are already approved: Gleevec, which inhibits Abl, and Iressa and Tarceva, which both inhibit EGFR, Sorafenib (Nexavar, BAY 43-9006) which inhibits Raf, Dasatinib (BMS-354825) and Nilotinib (AMN-107, Tasigna) which also inhibit Abl, Lapatinib which also inhibits EGFR, Temsirolimus (Torisel, CCI-779) which targets the mTOR pathway, Sunitinib (Stuten, SU11248) which inhibits several targets including VEGFR as well as specific antibodies inactivating kinase receptors: Herceptin and Avastin. The anti-EGFR agent can be selected from among Erlotinib, Cetuximab, Gefitinib, Zalutumimab, Panitumumab, Nimotuzumab, Matuzumab, Lapatinib, and is preferably Erlotinib or Cetuximab.

In a preferred embodiment, the additional antitumor drug is selected from Cisplatin, Dacarbazine, Fotemustine, Docetaxel and Cetuximab.

The term "therapy", as used herein, refers to any type of treatment of cancer (i.e., antitumor therapy), including an adjuvant therapy and a neoadjuvant therapy. Therapy comprises radiotherapy and therapies, preferably systemic therapies such as hormone therapy, chemotherapy, immunotherapy and monoclonal antibody therapy.

The term "adjuvant therapy", as used herein, refers to any type of treatment of cancer given as additional treatment, usually after surgical resection of the primary tumor, in a patient affected with a cancer that is at risk of metastasizing and/or likely to recur. The aim of such an adjuvant treatment is to improve the prognosis. Adjuvant therapies comprise radiotherapy and therapy, preferably systemic therapy, such as hormone therapy, chemotherapy, immunotherapy and monoclonal antibody therapy.

The term "hormone therapy" or "hormonal therapy" refers to a cancer treatment having for purpose to block, add or remove hormones. For instance, in breast cancer, the female hormones estrogen and progesterone can promote the growth of some breast cancer cells. So in these patients, hormone therapy is given to block estrogen and a non-exhaustive list of commonly used drugs includes: Tamoxifen, Toremifene, Anastrozole, Exemestane, Letrozole, Goserelin/Leuprolide, Megestrol acetate, and Fluoxymesterone. As used herein, the term "chemotherapeutic treatment" or "chemotherapy" refers to a cancer therapeutic treatment using chemical or biological substances, in particular using one or several antineoplastic agents.

The term "radiotherapeutic treatment" or "radiotherapy" is commonly used in the art to refer to multiple types of radiation therapy including internal and external radiation therapies or radioimmunotherapy, and the use of various types of radiation, including X-rays, gamma rays, alpha particles, beta particles, photons, electrons, neutrons, radio-isotopes, and other forms of ionizing radiation.

The term "therapeutical antibody" refers to any antibody having an anti-tumor effect. Preferably, the therapeutical antibody is a monoclonal antibody. Therapeutic antibodies are generally specific for surface antigens, e.g., membrane antigens. Most preferred therapeutic antibodies are specific for tumor antigens (e.g., molecules specifically expressed by tumor cells), such as CD20, CD52, ErbB2 (or HER2/Neu), CD33, CD22, CD25, MUC-1, CEA, KDR, αVβ3, and the like. The therapeutical antibodies include, but are not limited to, antibodies such as Trastuzumab (anti-HER2 antibody), Rituximab (anti-CD20 antibody), Alemtuzumab, Gemtuzamab, Cetuximab, Pertuzumab, Epratuzumab, Basiliximab, Daclizumab, Labetuzumab, Sevirumab, Tuvurimab, Palivizumab, Infliximab, Omalizumab, Efalizumab, Natalizumab, Clenoliximab, and Bevacizumab.

Hyperthermia is a medical treatment in which is exposed to high temperatures to damage and kill cancer cells or to make cancer cells more sensitive to the effects of radiation and certain anti-cancer drugs. There are many techniques, well-known by the one skilled in the art, by which heat may be delivered. Some of the most common involve the use of focused ultrasound (FUS or HIFU), infrared sauna, microwave heating, induction heating, magnetic hyperthermia, infusion of warmed liquids, or direct application of heat such as through sitting in a hot room or wrapping a patient in hot blankets.

FIGURES

FIG. 1: Toxicity assay of compound 1 (Cefprozil). Bars from left to right: $1^{st}$=control=untreated animals; $2^{nd}$=100 mg/kg; $3^{rd}$=200 mg/kg; $4^{th}$=300 mg/kg.

Figure 2:
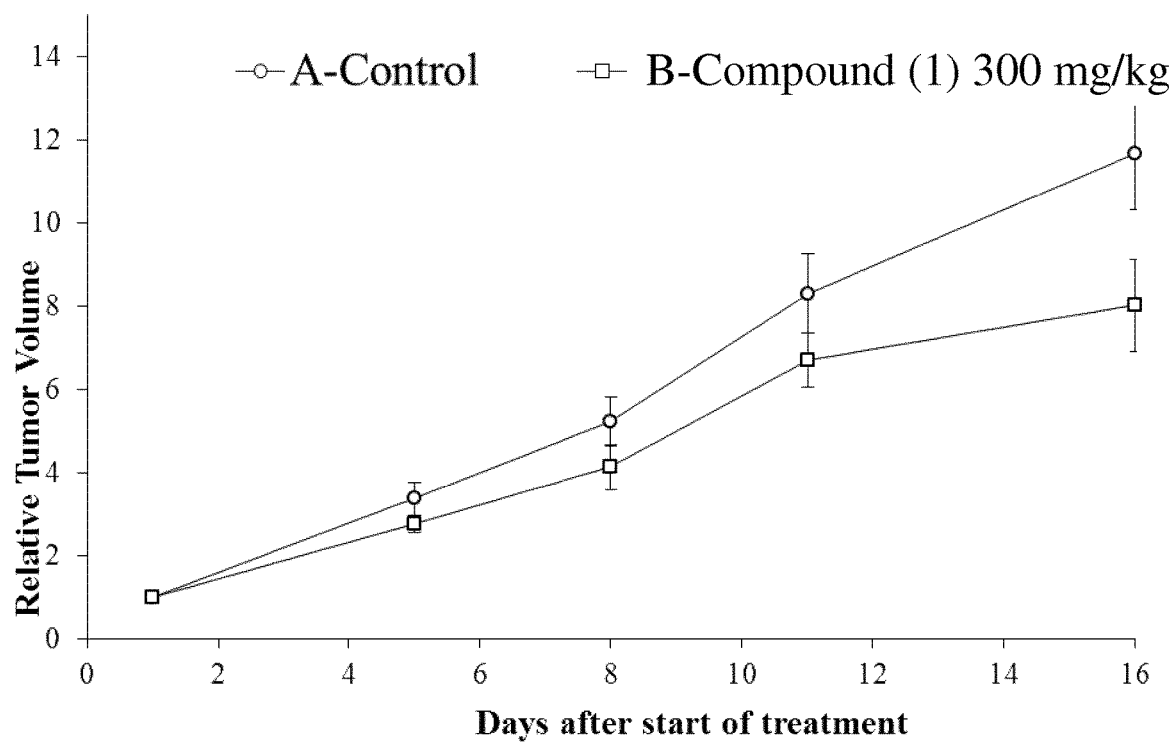

FIG. 2: Effect of compound 1 treatment on the growth of SC131 lung tumor.

Figure 3:
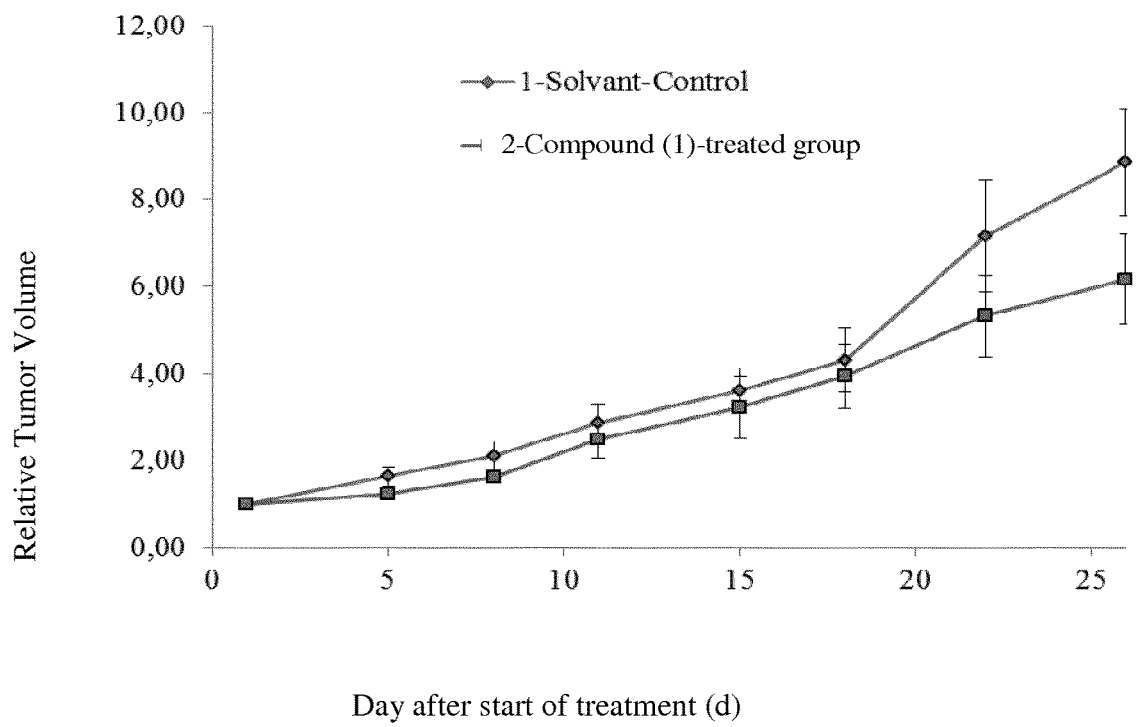

FIG. 3: Effect of compound 1 treatment on the growth of MP55B uveal tumor.

Figure 4:
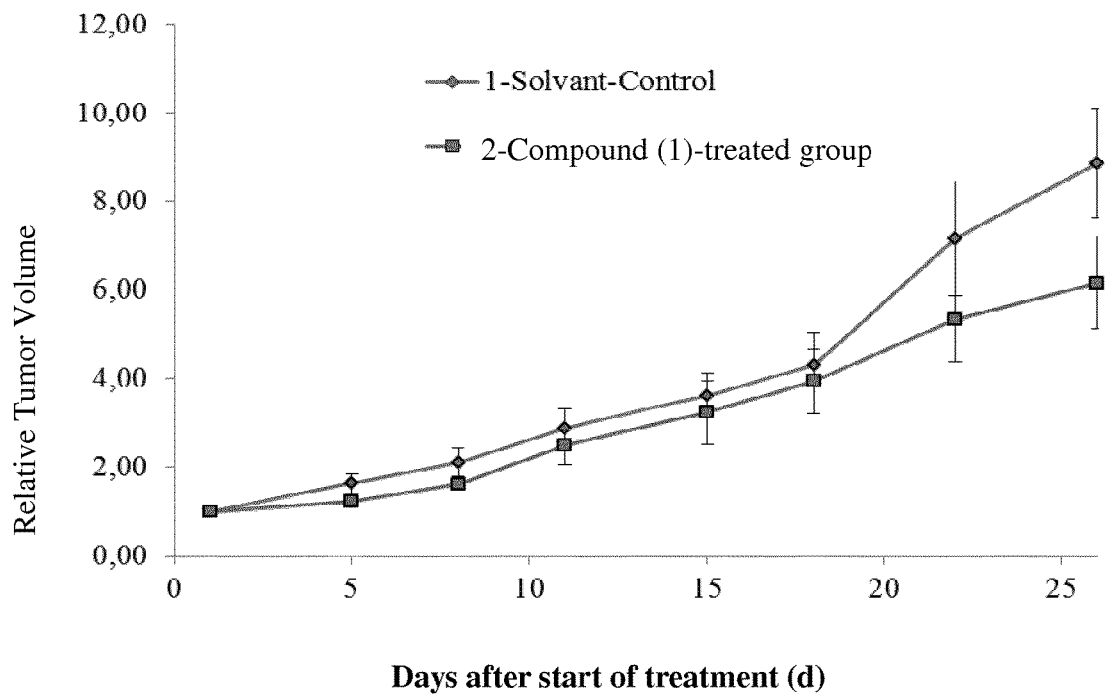

FIG. 4: Effect of compound 1 treatment on the growth of LCF 29 lung tumor.

Figure 5:
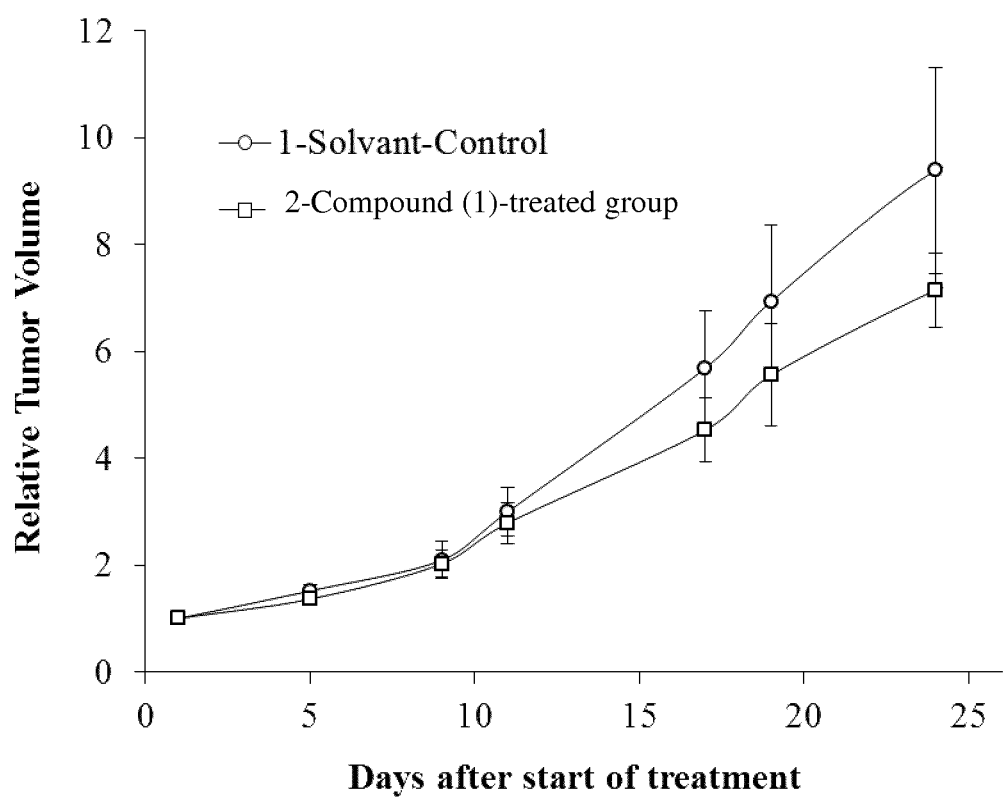

FIG. 5: Effect of compound 1 treatment on the growth of HBCx-12A breast tumor.

Further aspects and advantages of the invention will be disclosed in the following Examples section.

EXAMPLES

Example 1: In Vitro Assay of CXCR4 Antagonist Activity

Materials and Methods

The antagonist activity of compounds has been assessed with an in vitro assay with human CXCR4 receptor expressed in transfected CHO cells. It has been determined by measuring their effects on agonist-induced impedance modulation using the Cell-Key (Cellular Dielectric Spectroscopy) detection method.

The assay has been performed as detailed in Zhou, Y. et al. (J. Biol. Chem., 277, 49481-49487). Briefly, cells were seeded onto 96-well plates at $5 \times 10_4$ cells/well and allowed to grow overnight in standard growth media under standard culture conditions. Growth media was exchanged to HBSS buffer+20 mM HEPES (Invitrogen) with 10% FCS and 0.1% BSA, and cells were allowed to equilibrate for 45 min at 28° C. before the start of experiments. Plates were placed onto the system and measurements were made at a temperature of 28° C. HBSS (basal and stimulated controls), the reference antagonist MIP-II (IC50 determination) or the test compounds were preincubated for 15 minutes before the addition of HBSS (basal control) and the reference agonist SDF-1α at 1 nM (EC80). Impedance measurements were monitored for 10 minutes.

Compounds 1 and 2 of the invention have been purchased from AKSci and Vitas-M Laboratory, respectively. Compounds of WO 02/096430 have been purchased from Vitas-M Laboratory. Compound 3, for comparative tests, has been purchased from Vitas-M Laboratory.

Results

CXCR4 antagonist effect is disclosed in Table 1 below.

TABLE 1

| Compounds | Structure | CXCR4 antagonist effect (% inhibition) |
|---|---|---|
| 1 (Cefprozil) | 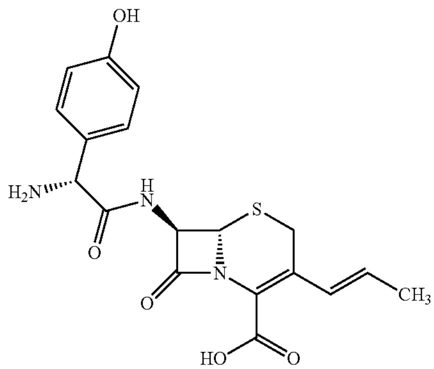 [SMILES: C/C=C/C1=C(C(=O)O)N2C(=O)[C@@H](NC(=O)[C@H](N)c3ccc(O)cc3)[C@@H]2SC1] | 38.2 |
| 2 | 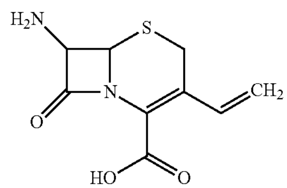 | 25.1 |
| WO 02/096430 Example 25 | 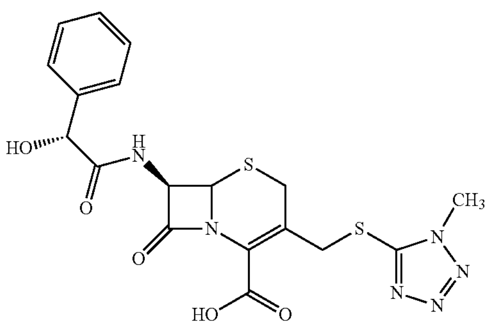 [SMILES: Cn1nnnc1SCC1=C(C(=O)O)N2C(=O)[C@@H](NC(=O)[C@H](O)c3ccccc3)C2SC1] | 16.5 |
| WO 02/096430 Example 283 | 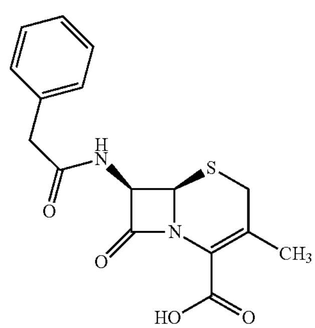 [SMILES: CC1=C(C(=O)O)N2C(=O)[C@@H](NC(=O)Cc3ccccc3)[C@H]2SC1] | 15.9 |
| WO 02/096430 Example 258 | 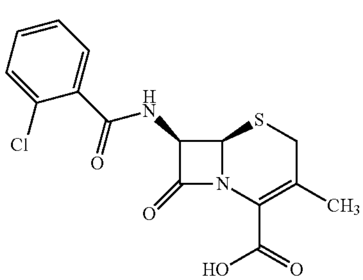 [SMILES: CC1=C(C(=O)O)N2C(=O)[C@@H](NC(=O)c3ccccc3Cl)[C@H]2SC1] | 3.2 |

TABLE 1-continued

| Compounds | Structure | CXCR4 antagonist effect (% inhibition) |
|---|---|---|
| WO 02/096430 Example 298 | 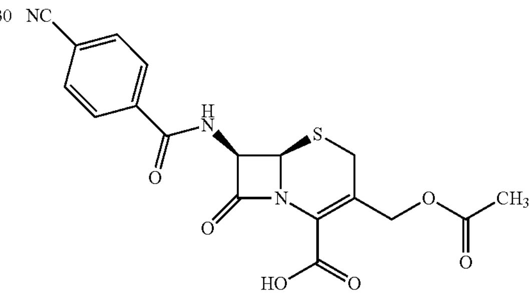 | 18.2 |
| 3 | 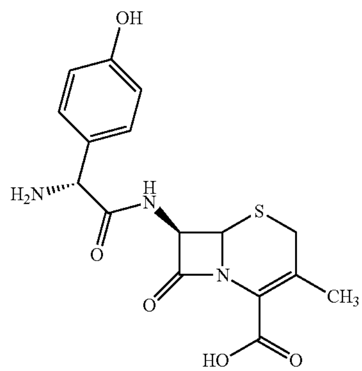 [SMILES: CC1=C(C(=O)O)N2C(=O)[C@@H](NC(=O)[C@H](N)c3ccc(O)cc3)C2SC1] | 14.2 |

The CXCR4 inhibition percentages of Cefprozil (1) and compound 2 are 38.2% and 25.1%, respectively, and demonstrate a significant CXCR4 antagonist effect since an acceptable CXCR4 inhibition percentage is above 20%.

Compounds of WO 02/096430 (examples 25, 258, 283 and 298), substituted at position 3 of the cephalosporin core by a methyl group, a sulfur-derivated group or an ethyl acetate group, have a CXCR4 inhibition percentage inferior to 20%, thereby demonstrating a non-significant CXCR4 antagonist effect.

The inventors have therefore demonstrated the importance of the alkylene group at position 3 of the cephalosporin core that characterizes the compounds of formula (I) of the invention having a significant CXCR4 antagonist effect.

This is confirmed by the comparative results between Cefprozil (1) and its methyl analog (3) substituted at position 3 of the cephalosporin core. Indeed, CXCR4 antagonist effect of Cefprozil (% inhibition=38.2) is significantly more important than the CXCR4 effect of the methyl analog (3) (14.2%).

Example 2: In Vivo Assay of Antitumor Activity

Materials, Models and Methods
Patient-Derived Xenografts (PDXs)

Establishment of tumor models, transplantation procedure and experimental therapeutic assays have already been published (Nemati et al., Clin Cancer Res. 2000 May: 2075-86).

One triple-negative breast cancer (BC) xenograft that developed spontaneous lung metastases, two non-small cell lung cancer (NSCLC) xenografts with or without EFGR gene mutation, and one uveal melanoma (UM) xenograft with GNA11 (Guanine Nucleotide Binding Protein (G Protein), Alpha 11) gene mutation have been selected for the present study. Molecular characteristics of these models are presented in the following table:

| Types of cancer | Names | Characteristics |
|---|---|---|
| NSCLC | SC131 | Adenocarcinoma mutated KRAS |
|  | LCF29 | Adenocarcinoma mutated EGFR |
| UM | MP55B | mutated GNA11 |
| BC | HBCx-12A | ER-, PR-, Her2- |

Animals and Housing

Swiss nu/nu (nude) female mice, 5 weeks old, were used as recipients of xenografts of BC and NSCLC. SCID female mice, 5 weeks old, were used as recipients of UM xenografts. Mice came from Charles River Laboratories. Mice were housed in group cages of 5 mice each. Food sterilized by hydrogen peroxide and disposable water bottles were provided ad libitum.

Methodology of Tumor Transplantation

The tumor material was cut into pieces of 5×5 mm. Each tumor fragments were implanted subcutaneously interscapular into anesthetized mice and identified by a number. These procedures were done in aseptic conditions, by skilled experimenters who respect the animals' welfare.

Inclusion Criteria and Randomization

Only tumor-bearing mice were randomly distributed into groups of 8-10 mice assigned as controls or treated. All treatments started at day one as the tumors reached a volume comprised between 50 mm$^3$ and 250 mm$^3$. In cases of heterogeneous tumor take and growth, inclusion of mice was delayed until tumors reached the initial optimal volume.

Tested Compound

Stock powder of Cefprozil (1) was sampled in daily doses and kept at 4° C. Cefprozil was suspended in glucose 5% and administrated per os.

Acquisition of Data

Tumor sizes were measured twice a week using a caliper. Two perpendicular diameters (a and b) were registered. Then individual tumor volumes were calculated as: $a \times b^2/2$ in $mm^3$, where a is the large diameter and b the small one.

Relative tumor volume (RTV) was calculated, as the ratio of the volume at the time t divided by the initial volume at day 1 and multiplied by 100. These data allow to rapidly evaluating the lack of growth when the RTV is equal to or less than 100% (tumor regressions). Curves of mean (or median) of RTV in treated group and control as a function of time are presented.

Weights of individual mice were measured twice a week. Variations of weight of mice as compared to their initial weight and means (or median) per group were calculated.

Samples

Mice were euthanatized when tumor volume was 2000 $mm^3$. Samples were taken from 5 mice per group. Tumor fragment and half lung were frozen, other tumor fragment and half lung were fixed in formalin for all models. Blood samples were additional for the UM models.

Results

1. Dose-Dependent Tolerance

Cefprozil (1) was administered as indicated in the following table.

| Groups | Doses | Administration schedule | Number of subject/group |
|---|---|---|---|
| Control | — | — | 5 |
| Cefprozil (1) | 100 mg/kg | 5 days/week | |
| Cefprozil (1) | 200 mg/kg | Per os | |
| Cefprozil (1) | 300 mg/kg | 3 weeks | |

Cefprozil was well tolerated at the dose 300 mg/kg per day and oral administration, 5 days a week (see FIG. 1).

No loss of weight or behavior troubles were observed during the treatment.

This result allowed designing the Cefprozil treatment for further in vivo experiments:

300 mg/kg per day by oral administration, 5 days a week, for 6 weeks.

2. Assessment of In Vivo Antitumor Effect

The following results were obtained:

NSCLC SC131 model: FIG. 2 and the following table

| Groups | N mice per group | V at start of experiment ($mm^3$ ± sd) | V at the end of experiment ($mm^3$ ± sd) | % TGI | CR |
|---|---|---|---|---|---|
| Control | 9 | 155 ± 18.35 | 1656 ± 140.09 | none | none |
| Cefprozil | 9 | 166 ± 15.53 | 1297 ± 203.16 | 31 | none |

Abbreviations: Tumor Growth Inhibition (TGI), Complete Remission (CR)

An in vivo tumor growth inhibition of 31% has been observed after Cefprozil (1) administration.

Uveal melanoma MP55B model: FIG. 3 and the following table

| Groups | N mice per group | V at start of experiment ($mm^3$ ± sd) | V at the end of experiment ($mm^3$ ± sd) | % TGI | CR |
|---|---|---|---|---|---|
| Control | 11 | 151 ± 37.28 | 1124 ± 195.40 | none | none |
| Cefprozil | 10 | 182 ± 35.10 | 962 ± 190.41 | 30 | none |

Abbreviations: Tumor Growth Inhibition (TGI), Complete Remission (CR)

An in vivo tumor growth inhibition of 30% has been observed after Cefprozil (1) administration.

NSCLC LCF29 model: FIG. 4 and the following table

| Groups | N mice per group | V at start of experiment ($mm^3$ ± sd) | V at the end of experiment ($mm^3$ ± sd) | % TGI | CR |
|---|---|---|---|---|---|
| Control | 10 | 72 ± 5.33 | 698 ± 111.38 | none | none |
| Cefprozil | 10 | 90 ± 7.90 | 574 ± 83.58 | 29 | none |

Abbreviations: Tumor Growth Inhibition (TGI), Complete Remission (CR)

An in vivo tumor growth inhibition of 29% has been observed after Cefprozil (1) administration.

BC HBCx-12A model: FIG. 5 and the following table

| Groups | N mice per group | V at start of experiment ($mm^3$ ± sd) | V at the end of experiment ($mm^3$ ± sd) | % TGI | CR |
|---|---|---|---|---|---|
| Control | 10 | 77 ± 9.10 | 735 ± 166.96 | none | none |
| Cefprozil | 10 | 73 ± 8.86 | 520 ± 66.46 | 20 | none |

Abbreviations: Tumor Growth Inhibition (TGI), Complete Remission (CR)

An in vivo tumor growth inhibition of 20% has been observed after Cefprozil (1) administration.

In conclusion, the inventors have shown that Cefprozil (1) induced tumor growth inhibition in the four above models, thereby demonstrating the therapeutic effect of the compound of the formula (I) for treating cancer, in particular breast cancer, lung cancer and uveal melanoma.

The invention claimed is:

1. A method for treating a cancer in a subject in need thereof comprising administering to said subject an effective amount of 7-(2-amino-2-(4-hydroxyphenyl)acetamido)-8-oxo-3-(prop-1-enyl)-5-thia-1-azabicyclo[4.2.0]oct-2-ene-carboxylic acid or a pharmaceutically acceptable salts thereof or a pharmaceutical composition comprising said compound or a pharmaceutically acceptable salt thereof, wherein said cancer is selected from the group consisting of breast cancer, lung cancer, and melanoma.

2. The method according to claim 1, wherein the compound is formulated in an extended-release, controlled-release or sustained-release pharmaceutical composition.

3. The method according to claim 2, wherein the extended-release, controlled-release or sustained-release pharmaceutical composition comprises one or more carbomers.

4. The method according to claim 1, said method further comprising the administration of at least one additional antitumor drug to said subject.

5. The method according to claim 4, wherein the additional antitumor drug is selected from the group consisting of an antimitotic agent, an inhibitor of topoisomerases I or II, a DNA alkylating agent, an anti-metabolic agent, a kinase inhibitor, an anti-EGFR agent and a therapeutic antibody.

6. The method according to claim 4, wherein the additional antitumor drug is selected from the group consisting of
   a) a DNA alkylating agent selected from the group consisting of cisplatin, carboplatine, fotemustine, oxaliplatine and dacarbazine;
   b) an antimitotic agent selected from the group consisting of docetaxel and paclitaxel; and
   c) an anti-EGFR agent selected from the group consisting of erlotinib, cetuximab, gefitinib, zalutumimab, panitumumab, nimotuzumab, matuzumab, and lapatinib.

7. The method according to claim 1, said method comprising a combination treatment of radiotherapy, hyperthermia and/or other antitumor therapies selected from the group consisting of hormone therapy, chemotherapy, immunotherapy and monoclonal antibody therapy, optionally before, simultaneously and/or after tumor surgery and treatment with the compound of formula (I).

8. The method according to claim 1, wherein said cancer is melanoma.

9. The method according to claim 1, wherein said cancer is breast cancer.

10. The method according to claim 8, wherein said melanoma is uveal melanoma.

11. The method according to claim 1, wherein said lung cancer is selected from small-cell lung cancer or non-small cell lung cancer.

12. The method according to claim 1, wherein said breast cancer is a triple-negative breast cancer.

13. The method according to claim 1, wherein said cancer is lung cancer.

14. The method according to claim 1, wherein 7-(2-amino-2-(4-hydroxyphenyl)acetamido)-8-oxo-3-(prop-1-enyl)-5-thia-1-azabicyclo[4.2.0]oct-2-ene-carboxylic acid or a pharmaceutically acceptable salt thereof is administered to said subject.

15. The method according to claim 1, wherein a pharmaceutical composition comprising 7-(2-amino-2-(4-hydroxyphenyl)acetamido)-8-oxo-3-(prop-1-enyl)-5-thia-1-azabicyclo[4.2.0]oct-2-ene-carboxylic acid or a pharmaceutically acceptable salt thereof is administered to said subject.

* * * * *

UNITED STATES PATENT AND TRADEMARK OFFICE
CERTIFICATE OF CORRECTION

PATENT NO. : 10,821,114 B2  
APPLICATION NO. : 15/301462  
DATED : November 3, 2020  
INVENTOR(S) : Arnaud Sinan Karaboga et al.

Page 1 of 1

It is certified that error appears in the above-identified patent and that said Letters Patent is hereby corrected as shown below:

In the Claims

Column 20,  
Line 56, "acceptable salts" should read --acceptable salt--.

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*